(12) United States Patent
Ramsey et al.

(10) Patent No.: US 12,721,579 B2
(45) Date of Patent: Sep. 1, 2026

(54) BREAST AXILLA AND THYROID RADIATION SHIELDING DEVICE FOR MEDICAL PERSONNEL

(71) Applicant: ProtectMed, LLC, Dallas, TX (US)

(72) Inventors: Lauren Ramsey, Fort Worth, TX (US); Chet Rees, Dallas, TX (US); Ryan Baldwin, Seattle, WA (US)

(73) Assignee: ProtectMed, LLC, Dallas, TX (US)

( * ) Notice: Subject to any disclaimer, the term of this patent is extended or adjusted under 35 U.S.C. 154(b) by 331 days.

(21) Appl. No.: 18/405,001

(22) Filed: Jan. 5, 2024

(65) Prior Publication Data

US 2024/0225571 A1 Jul. 11, 2024

Related U.S. Application Data

(60) Provisional application No. 63/478,554, filed on Jan. 5, 2023.

(51) Int. Cl.
*A61B 6/10* (2006.01)
*G21F 3/025* (2006.01)

(52) U.S. Cl.
CPC .............. *A61B 6/107* (2013.01); *G21F 3/025* (2013.01)

(58) Field of Classification Search
CPC . A61B 6/107; G21F 3/025; G21F 3/02; G21F 3/03
See application file for complete search history.

(56) References Cited

U.S. PATENT DOCUMENTS 2,642,542 A * 6/1953 Weinberg .................. G21F 3/03 2/81
3,164,840 A * 1/1965 Reynolds ................ G21F 3/025 2/457

(Continued)

FOREIGN PATENT DOCUMENTS

WO WO-8700342 A * 1/1987 ............... G21F 3/02
WO WO-2006015695 A2 * 2/2006 ............... G21F 3/02
WO WO-2013039195 A1 * 3/2013 ............... G21F 3/02

OTHER PUBLICATIONS

Annual Product Catalog Hospidis. Catalog [online]. INFAB 2021. Retrieved from the Internet: <URL: www.INFABCORP.com> on Dec. 10, 2025 (6 pgs.).

(Continued)

*Primary Examiner* — David A Vanore
(74) *Attorney, Agent, or Firm* — Harper & Bates LLP; Shannon W. Bates

(57) ABSTRACT

A radiation shielding device to be worn in conjunction with a radiation standard apron includes a first shielded portion configured to cover the right axilla and the outer quadrants of the right breast of a user with shielding material, a second shielded portion configured to cover the left axilla and the outer quadrants of the left breast of a user with shielding material, a first arm sleeve coupled to the first shielded portion and configured to cover an underside portion of a right proximal arm of a user with shielding material, a second arm sleeve coupled to the second shielded portion and configured to cover an underside portion of a left proximal arm of a user with shielding material, and a plurality of lightweight material portions coupling the first shielded portion and the second shielded portion.

24 Claims, 8 Drawing Sheets

(56) References Cited

U.S. PATENT DOCUMENTS 3,996,620 A * 12/1976 Maine ........................ G21F 3/02 2/457
4,196,355 A * 4/1980 Maine .................... A61B 6/107 250/516.1
5,115,140 A * 5/1992 Rodriguez ................ G21F 3/02 2/457
5,274,851 A * 1/1994 Simpkins, Sr. ......... A61F 5/028 2/92
5,419,342 A * 5/1995 Scott ......................... G21F 3/02 128/849
5,690,537 A * 11/1997 Kalmus .................... A41C 3/10 450/55
8,067,759 B1 * 11/2011 Swartz ...................... G21F 3/02 2/92
8,350,241 B2 * 1/2013 Bustamante Grant ....................... A61B 6/107 250/516.1
8,710,477 B1 * 4/2014 Marchione ......... A41D 13/0025 2/457
11,028,505 B1 * 6/2021 Lambert ................ A41D 31/26
2004/0149938 A1 * 8/2004 Grilliot ..................... G21F 3/02 250/516.1
2005/0211930 A1 * 9/2005 DeMeo ..................... G21F 3/02 250/516.1
2007/0138415 A1 * 6/2007 Rees ...................... A61B 6/107 250/516.1
2009/0114857 A1 * 5/2009 DeMeo ..................... G21F 1/00 250/516.1
2009/0126088 A1 * 5/2009 Yadav .................... A41D 13/02 2/457
2009/0184269 A1 * 7/2009 Rees ...................... A61B 6/107 250/516.1
2012/0132217 A1 * 5/2012 Rees .................... A61B 6/4423 128/849
2013/0306824 A1 * 11/2013 Miller ................ A41D 13/0002 248/342
2014/0367594 A1 * 12/2014 Reynolds ............... A41D 27/18 250/516.1
2015/0287488 A1 * 10/2015 Glickman .............. A41D 13/04 250/516.1
2016/0317110 A1 * 11/2016 Rees ......................... G21F 3/00
2020/0194138 A1 * 6/2020 Glickman .............. A61B 6/107
2020/0219632 A1 * 7/2020 Naidu ....................... B32B 5/26
2020/0258645 A1 * 8/2020 Watson .............. A41D 13/0002
2021/0082592 A1 * 3/2021 Johnson .................... G21F 3/02
2021/0145090 A1 * 5/2021 Sintay .................. A61N 5/1077
2022/0000193 A1 * 1/2022 Monier ................... G21F 3/025
2024/0225571 A1 * 7/2024 Westcott ................. G21F 3/025
2025/0292925 A1 * 9/2025 Mayberry ............... G21F 3/025

OTHER PUBLICATIONS

Radiation Safety. Catalog [online]. Protech Medical, 2020. Retrieved from the Internet: <URL: https://static1.squarespace.com/static/58ae1e0129687f2929bd0517/t/6122f4cd66a11803f61842c4/1629680855008/Protech+Catalog+2020.pdf> on Dec. 10, 2025 (7 pgs.).

Instagram post entitled "Looking for an ultra lightweight . . . ", posted Mar. 5, 2018 by user "protechmedical". Retrieved from Instagram on Nov. 20, 2025 (1 pg.).

Radiation Protection Aprons and Accessories. Catalog [online]. Burlington Medical. Retrieved from the Internet: <URL: https://burlington-medical. paperturn-view.com/main-wearables-catalog?pid=Mjk295387&p=28&v=8.3> on Nov. 11, 2025 (5 pgs.).

Apron Catalog. Catalog [online]. Barrier Technologies, 2025. Retrieved from the Internet: <URL: https://barriertechnologies.com/pdfs/Barrier-Technologies-Radiation-Protection-Aprons.pdf> on Nov. 11, 2025 (6 pgs.).

Instagram post entitled "Ultraflex Dental X-ray Aprons", posted Jun. 19, 2020 by user "barriertechnologies". Retrieved from Instagram on Dec. 10, 2025 (1 pg.).

EN RA637 Bolero. Brochure [online]. Mavig. Retrieved from the Internet: <URL: https://mavig.com/product/bolero-ra637/> on Dec. 10, 2025 (1 pg.).

Instagram post entitled "BOLERO RA637", posted Aug. 25, 2021 by user "mavig_international". Retrieved from Instagram on Nov. 20, 2025 (2 pgs.).

Innovative Quality Solutions for Medical Imaging. Catalog [online]. AADCO 2019. Retrieved from the Internet: <URL: https://pdf.medicalexpo.com/pdf/aadco-medical/aadco-medical-2019-catalog/81034-222564.html> on Dec. 10, 2025 (3 pgs.).

* cited by examiner

BREAST AXILLA AND THYROID RADIATION SHIELDING DEVICE FOR MEDICAL PERSONNEL

CROSS-REFERENCE TO RELATED APPLICATIONS

This application claims the benefit of U.S. Provisional Patent Application Ser. No. 63/478,554, filed Jan. 5, 2023 and entitled "Breast Axilla and Thyroid Radiation Shielding Device for Medical Personnel", which is incorporated herein by reference for all purposes.

TECHNICAL FIELD

The present disclosure relates to radiation shielding devices, and more particularly, to radiation shielding devices comprising garments designed to shield those portions of the upper body left exposed by standard radiation aprons. The present disclosure also relates to methods of radiation shielding by radiation shielding devices worn in conjunction with standard radiation aprons.

BACKGROUND

Medical personnel often wear protective garments with radiation shielding, such as standard radiation aprons. However, conventional radiation shielding garments do not provide sufficient radiation shielding to all portions of the upper body that may be exposed to radiation, thereby increasing the risk of cancer to medical personnel.

SUMMARY

The present disclosure is directed to various implementations of radiation shielding devices designed for use with standard radiation aprons.

In one implementation, a radiation shielding device includes a first shielded portion configured to cover and protect the right axilla and the outer quadrants of the right breast of a user, and a second shielded portion configured to cover and protect the left axilla and the outer quadrants of the left breast of a user. The first shielded portion and the second shielded portion may further be configured to cover and protect the shoulders of a user and/or a portion of the back of a user.

The radiation shielding device may further include a first sleeve coupled to the first shielded portion and a second sleeve coupled to the second shielded portion. The first sleeve and the second sleeve each include radiation shielding material configured to protect at least a portion of the proximal arms of a user from radiation, including the underside portions of the proximal arms of a user. In some implementations, a first adjustment strap is coupled to the first sleeve and a second adjustment strap is coupled to the second sleeve to enable the user to adjust the width of each sleeve opening.

The first shielded portion and the first sleeve may provide uninterrupted coverage of the right axilla, the outer quadrants of the right breast, and the underside portion of the right proximal arm of a user with shielding material. The second shielded portion and the second sleeve may provide uninterrupted coverage of the left axilla, the outer quadrants of the left breast, and the underside portion of the left proximal arm of a user with shielding material.

The radiation shielding device may further include a third shielded portion configured to cover and protect a portion of the chest of a user, a portion of the neck of a user in the thyroid region, or both. The third shielded portion may be fully removable from the radiation shielding device, or the third shielded portion may be tethered to another portion of the radiation shielding device, or the third shielded portion may be integrally formed with another portion of the radiation shielding device.

The radiation shielding device may further comprise a plurality of lightweight material portions that couple the first shielded portion to the second shielded portion. The plurality of lightweight material portions may further couple the third shielded portion to the first and/or the second shielded portions. In some implementations, the lightweight material portions are configured to cover portions of the torso of a user. The lightweight material portions may include a first front lightweight material portion, a second front lightweight material portion, and a back lightweight material portion. The lightweight material portions may be formed of a mesh material, a flexible material, or a combination thereof.

In some implementations, at least one of the first shielded portion, the second shielded portion, the first sleeve, the second sleeve, and the third shielded portion may be formed of small, overlapping segments of shielding material.

The details of one or more implementations of a radiation shielding device and associated methods are set forth in the accompanying drawings and the description below. Other features, objects, and advantages of the implementations will be apparent from the description and drawings.

BRIEF DESCRIPTION OF THE DRAWINGS

For a more complete understanding of this disclosure and its features, reference is now made to the following description, taken in conjunction with the accompanying drawings, in which.

Like reference symbols in the various drawings indicate like elements.

DETAILED DESCRIPTION

Medical personnel are routinely exposed to radiation and wear protective garments with radiation shielding, such as standard radiation aprons, but these garments do not provide sufficient protection to all areas of the upper body of the user, including but not limited to the areas of the proximal arms, the upper outer quadrant of the breast, and the sides of the user. These areas are exposed to radiation as the user moves to perform various tasks. As a result, female operating room personnel have a higher rate of breast cancer than the general population. Ionizing radiation is a known risk factor for cancer in humans, and many procedures in modern operating rooms involve this type of radiation.

Shielded arm sleeves are available that can be attached to standard radiation aprons, but these shielded arm sleeves do not provide sufficient protection for the areas of the upper outer quadrant of the breast and the sides of the user. In addition, these shielded arm sleeves usually attach separately to each side of standard radiation aprons, and are therefore out of balance, and require secure attachments to the standard radiation aprons. Due to these secure attachments, when a user wears conventional shielded arm sleeves, they tend to pull on the standard radiation aprons, making them uncomfortable and inhibiting freedom of movement. Shielded arm sleeves are also not compatible with all apron types.

Figure 1:
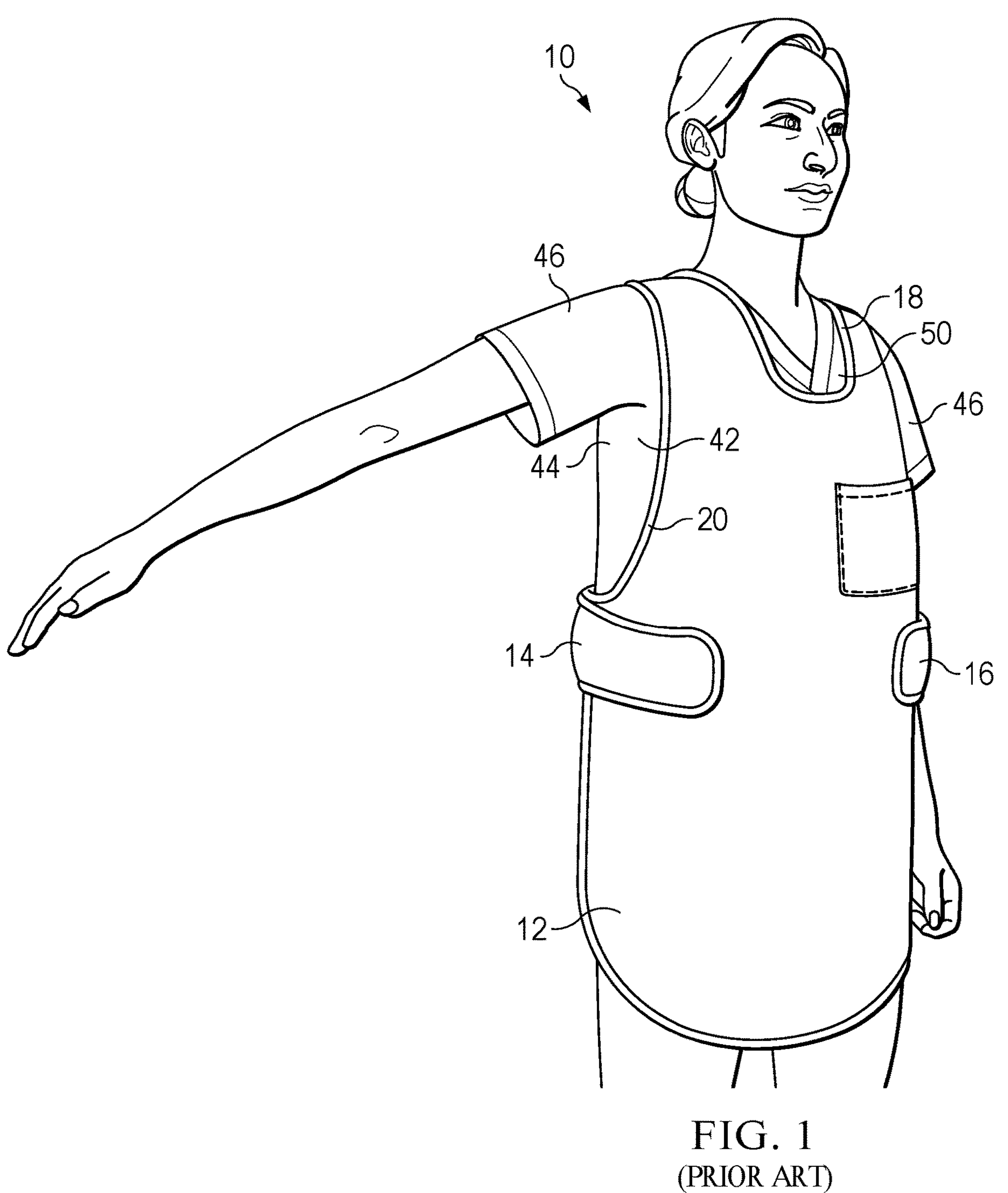
FIG. 1 illustrates a side perspective view of a user wearing a prior art standard radiation apron.

Referring now to the drawings, where like reference numerals represent like components, to protect from exposure to radiation, most medical personnel wear radiation shielding garments over their clothing, such as the prior art standard radiation apron 10 shown in FIG. 1. This apron 10 includes a front shielded portion 12 that fits over the user's shoulders and covers most of the user's torso and upper legs. The apron 10 further includes a first adjustable band 14 and a second adjustable band 16 that wrap around the user's torso and couple to the front shielded portion 12 to secure the apron 10 around the user.

As depicted in FIG. 1, the standard radiation apron 10 leaves the arms 46 of the user exposed. The standard radiation apron 10 also has large arm opening 20 and a large neck opening 18 that leave the axilla 44, the outer quadrants of the breast 42, the neck 48, and part of the chest 50 of the user exposed.

Figure 2:
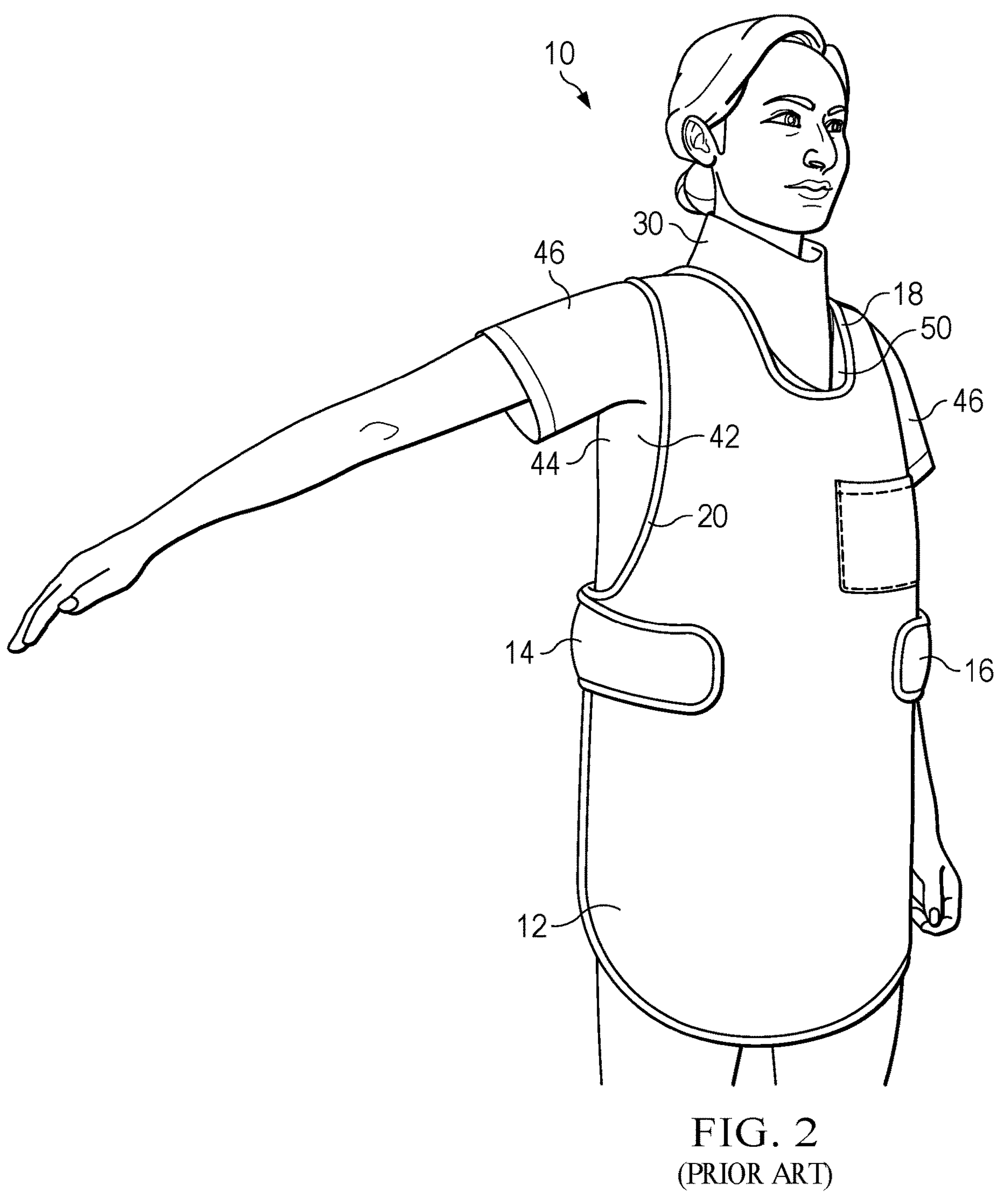
FIG. 2 illustrates a side perspective view of a user wearing the prior art standard radiation apron of FIG. 1 and a prior art thyroid guard.

Referring now to FIG. 2, radiation exposure may be improved by using a prior art thyroid guard 30 in conjunction with the standard radiation apron 10 shown in FIG. 1, but the neck opening 18 is often large enough that even with a standard thyroid guard 30, a portion of the chest 50 of the user remains exposed. The lack of radiation protection provided to the proximal arms 46, the axillae 44, the outer quadrants of the breast 42, and the chest 50 expose the user to higher risks of cancer.

The present disclosure relates to radiation shielding devices comprising garments designed to shield those portions of the upper body left exposed by standard radiation aprons. The present disclosure also relates to methods of radiation shielding by radiation shielding devices worn in conjunction with standard radiation aprons.

These radiation shielding devices may be worn by medical personnel to provide additional protection to the areas of the proximal arm, the breast, the axilla, the chest, and/or the thyroid while they are exposed to radiation associated with medical procedures.

The radiation shielding devices of the present disclosure include the same types of shielding material used in standard radiation aprons and conventional shielded arm sleeves. However, the radiation shielding devices of the present disclosure are more comfortable, more flexible, and permit more freedom of movement than conventional shielded arm sleeves. This is due, in part, to the radiation shielding devices not being attached, either fixedly or removably, to standard radiation aprons. Instead, these radiation shielding devices are separate garments designed to be worn over or under existing protective garments, such as standard radiation aprons, to provide additional protection against ionizing radiation. As such, the radiation shielding devices of the present disclosure can slide separately over or under standard radiation aprons, allowing more freedom of movement.

Figure 3:
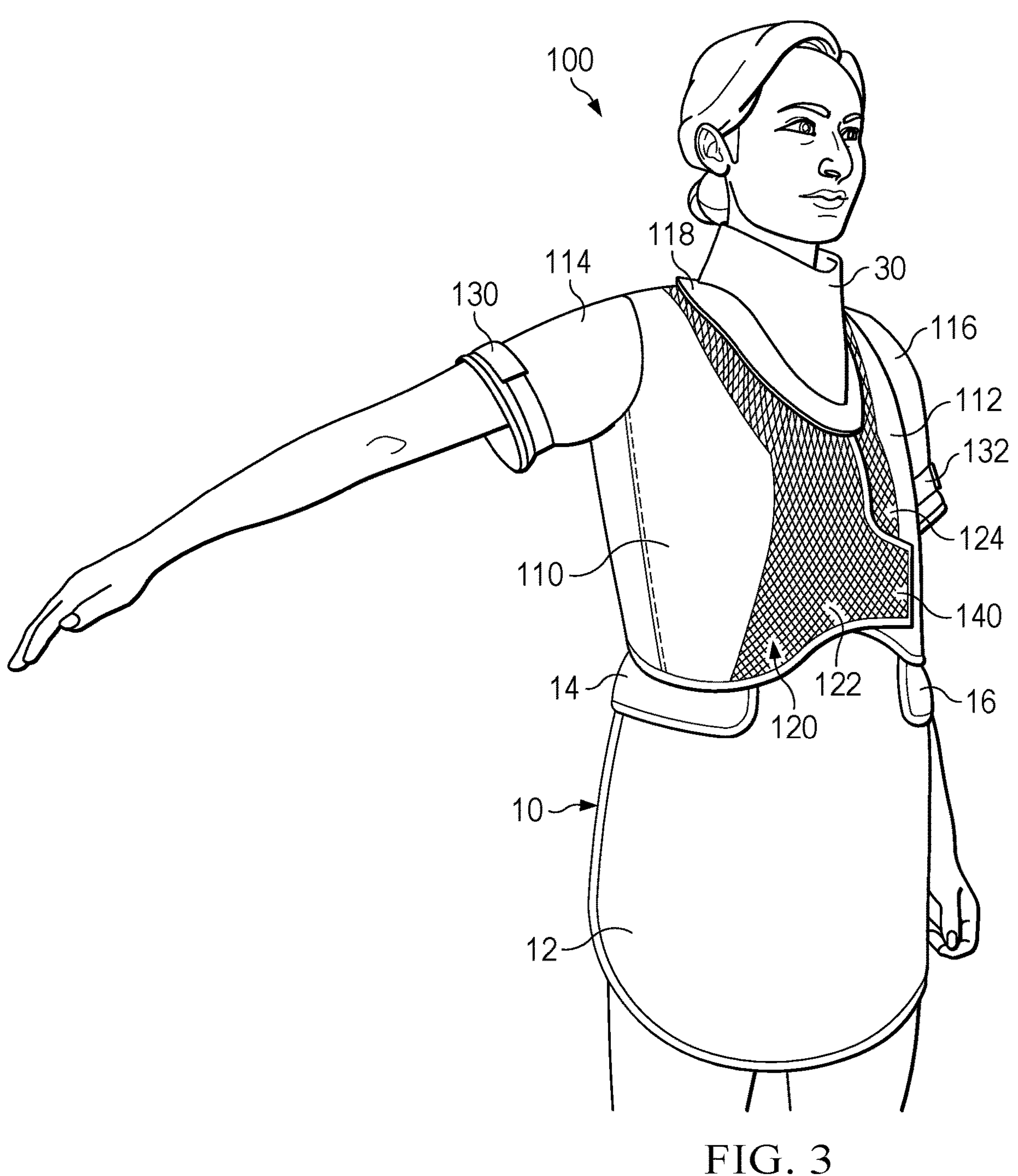
FIG. 3 illustrates a side perspective view of a user wearing one implementation of a radiation shielding device according to the present disclosure, in conjunction with the prior art standard radiation apron and thyroid guard of FIG. 2.
Figure 4:
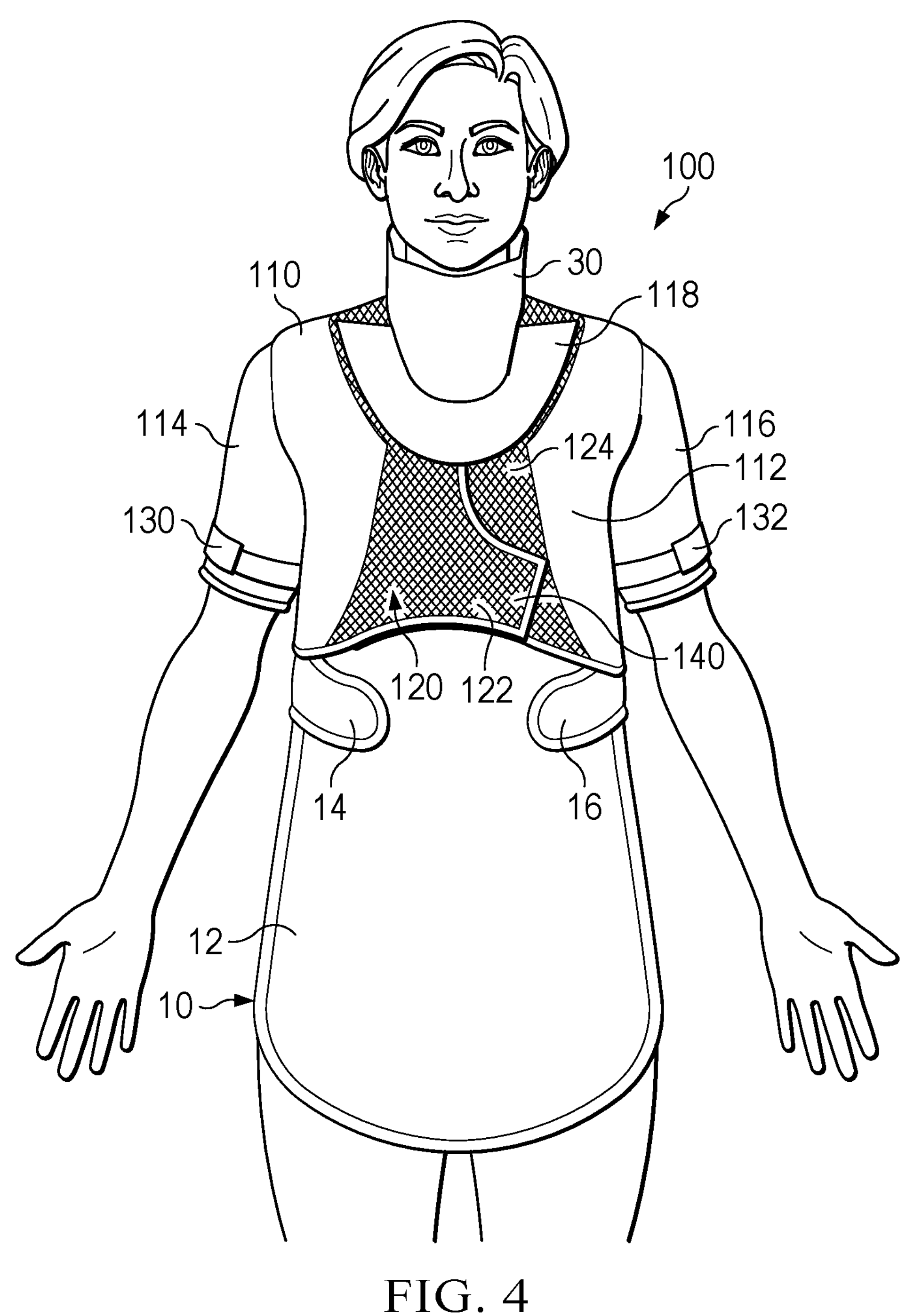
FIG. 4 illustrates a front plan view of a user wearing the radiation shielding device of FIG. 3, in conjunction with the prior art standard radiation apron and thyroid guard of FIG. 2.
Figure 5:
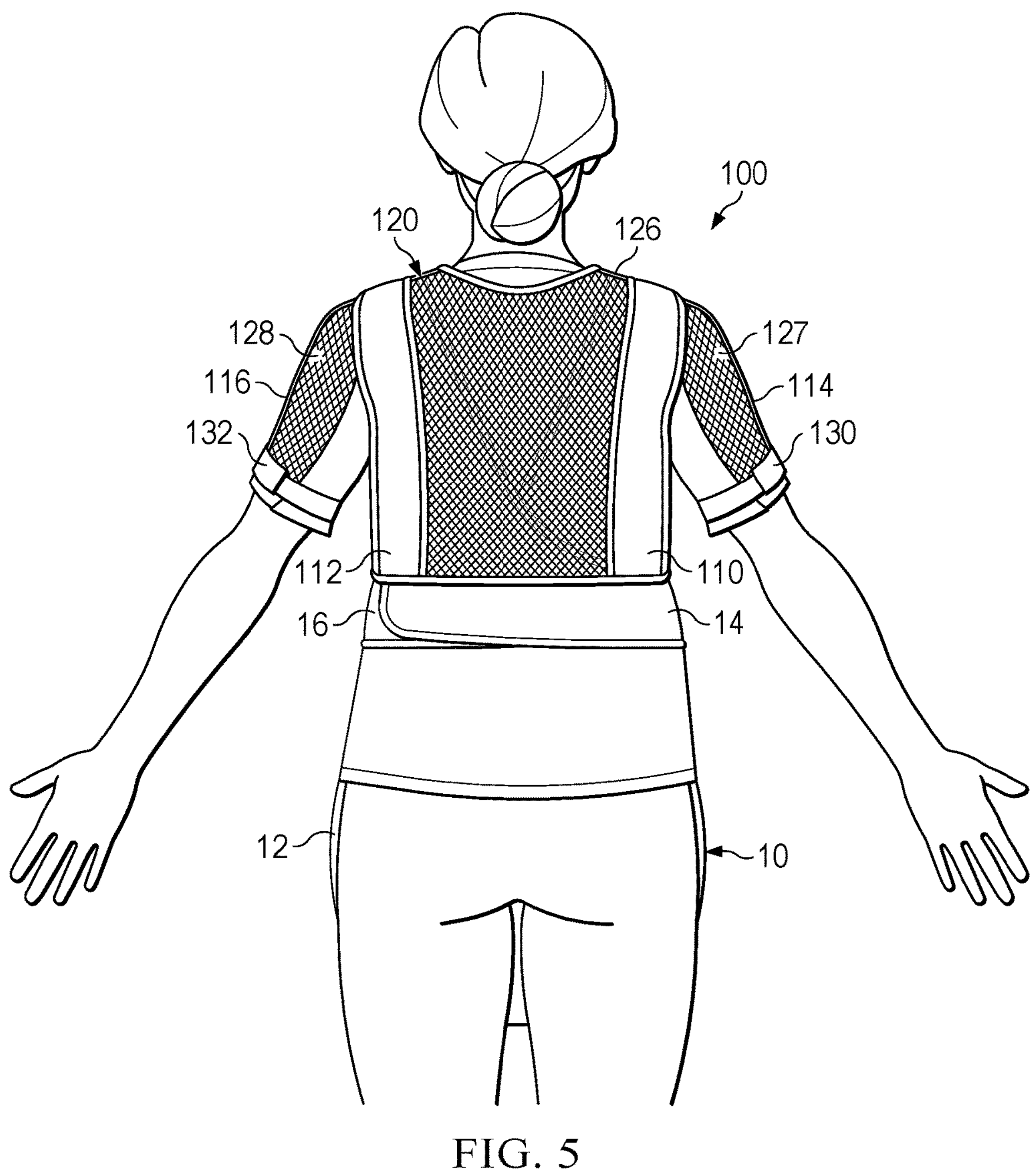
FIG. 5 illustrates a back plan view of a user wearing the radiation shielding device of FIG. 3, in conjunction with the prior art standard radiation apron and thyroid guard of FIG. 2.

FIG. 3 through FIG. 5 depict a side perspective view, a front plan view, and a back plan view, respectively, of a user wearing one implementation of a radiation shielding device 100 according to the present disclosure, in conjunction with the prior art standard radiation apron 10 and thyroid guard 30 of FIG. 2.

The radiation shielding device 100 includes a first shielded portion 110 configured to cover and protect the right axilla, the outer quadrants of the right breast, and a portion of the right chest of the user, and a second shielded portion 112 configured to cover and protect the left axilla, the outer quadrants of the left breast, and a portion of the left chest of the user. The first shielded portion 110 and the second shielded portion 112 may further be configured to cover and protect a portion of the shoulders of a user and/or a portion of the back of a user.

The radiation shielding device 100 may further include a first sleeve 114 coupled to the first shielded portion 110 and a second sleeve 116 coupled to the second shielded portion 112. The first sleeve 114 and the second sleeve 116 each include radiation shielding material configured to protect at least a portion of the proximal arms of a user from radiation. In some implementations, a first adjustment strap 130 is coupled to the first sleeve 114 and a second adjustment strap 132 is coupled to the second sleeve 116 to enable the user to adjust the width of each sleeve opening.

As shown, the first shielded portion 110, the second shielded portion 120, the first sleeve 114, and the second sleeve 116 provide complete coverage to protect the axilla 44 and the underside of the proximal arms 46 of the user. Since the user is normally facing the radiation scatter source during procedures, and radiation scatter comes mostly in an upward direction from below, this complete coverage of shielding material provides protection to the user that is not found in prior art designs, which leave openings in the underside of the proximal arms 46 and the axilla 44.

The radiation shielding device 100 may further include a third shielded portion 118 configured to cover and protect a portion of the chest 50 of the user, covering the gap between the neck opening 18 in the standard radiation apron 10, as shown in FIG. 2. In various implementations, the third shielded portion 118 may be attached but fully removable from the radiation shielding device 100, or the third shielded portion may be tethered to another portion of the radiation shielding device 100, or the third shielded portion 118 may be integrally formed with another portion of the radiation shielding device 100.

In some implementations, the radiation shielding device 100 uses shielding material in the first, second and third shielded portions 110, 112, 118 that attenuates ionizing radiation associated with medical imaging. This shielding material is enclosed in fabric, so the shielding material acts as a liner in the garment.

The radiation shielding device 100 further includes a plurality of lightweight material portions 120. When referring to lightweight material portions 120 in the present disclosure, the term "lightweight" indicates that the material portions 120 are relatively lighter in weight than the shielded portions. The lightweight material portions 120 may include a first front lightweight material portion 122, a second front lightweight material portion 124, and a back lightweight material portion 126 configured to cover portions of the torso of a user. These lightweight material portions 122, 124, and 126 couple the first shielded portion 110 to the second shielded portion 112 to form the garment 100. The plurality of lightweight material portions 120 may further couple the third shielded portion 118 to the first shielded portion 110 and/or the second shielded portion 112. In some implementations, the first sleeve 114 includes a lightweight material portion 127 on the back of the first sleeve 114, and the second sleeve 116 includes a lightweight material portion 128 on the back of the second sleeve 116, but lightweight material portions are not used on the parts of the sleeves 114, 116 that cover the underside of the proximal arms 46, which ensures that area is protected from radiation scatter.

The radiation shielding device 100 may be secured at the front with a closure 140, such as a hook and loop arrangement, buttons, snaps, zippers, or similar closure mechanisms. In some implementations, the first front lightweight material portion 122 overlaps the second front lightweight material portion 124 as shown in FIG. 3 and FIG. 4 when the closure 140 is fastened. In some implementations, the closure 140 is adjustable such that the lightweight material portions 120 and the adjustable closure 140 enable modifications to the size and shape of the garment 100, allowing the user freedom of movement. The lightweight material portions 120 lighten the weight of the radiation shielding device 100, provide breathability to the garment, and allow the first shielded portion 110, the second shielded portion 112, and the third shielded portion 118 to stay in place as the user moves. In some implementations, the lightweight material portions 120 are formed of a mesh material, a flexible material, or a combination thereof.

Figure 6:
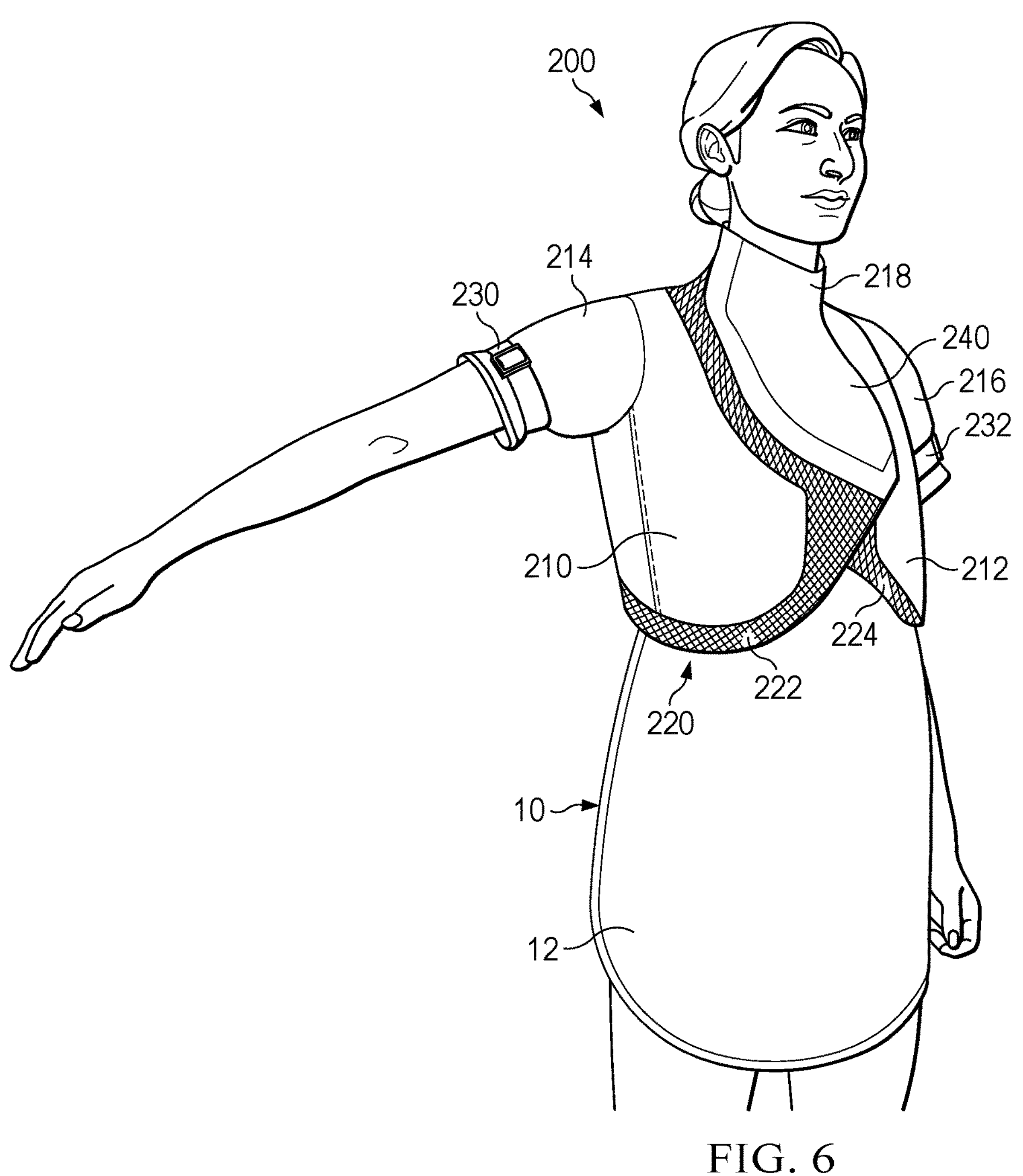
FIG. 6 illustrates a side perspective view of a user wearing another implementation of a radiation shielding device according to the present disclosure, in conjunction with the prior art standard radiation apron of FIG. 1.
Figure 7:
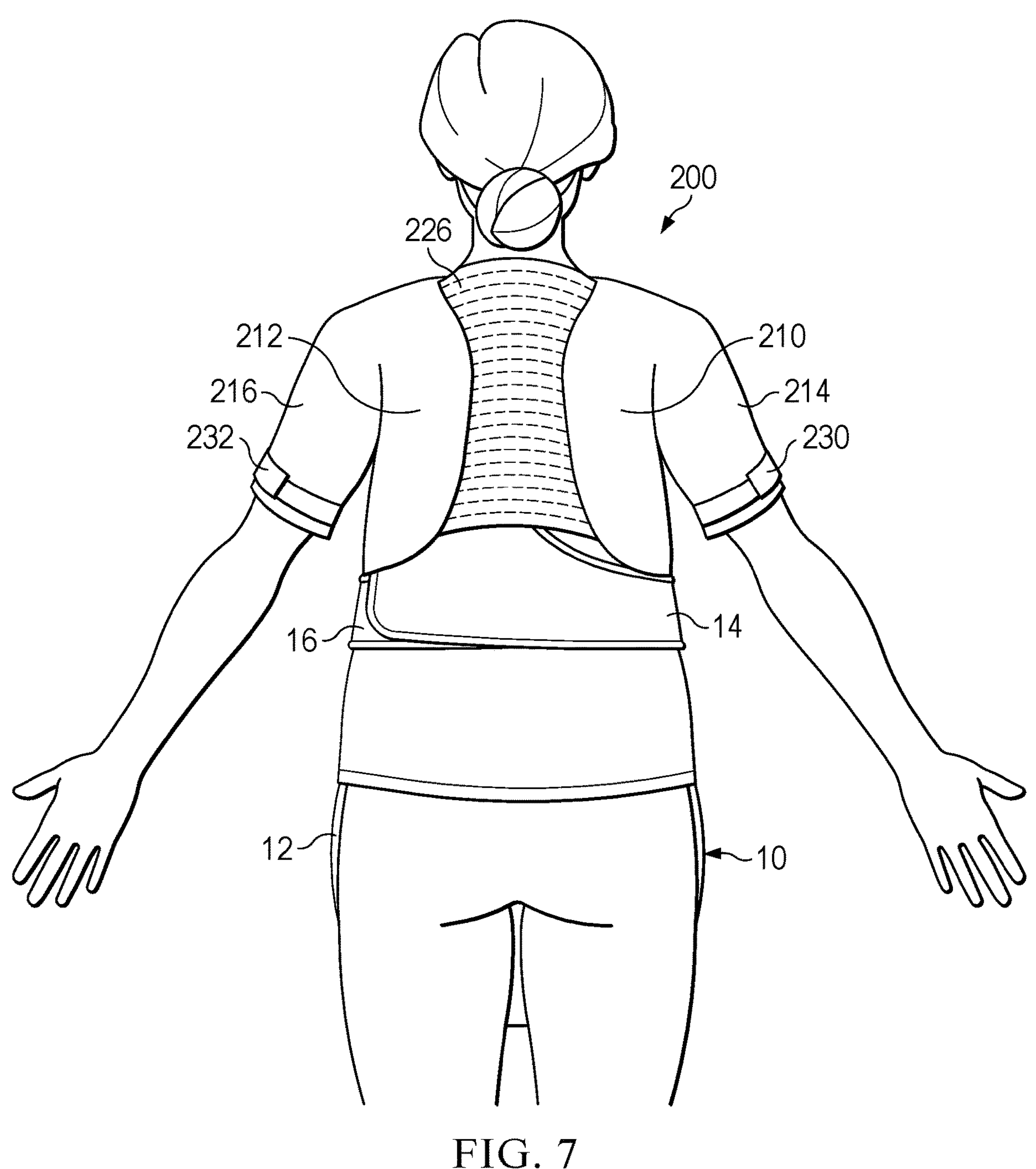
FIG. 7 illustrates a back plan view of a user wearing the radiation shielding device of FIG. 6, in conjunction with the prior art standard radiation apron of FIG. 1.

FIG. 6 and FIG. 7 depict a side perspective view and a back plan view, respectively, of a user wearing another implementation of a radiation shielding device 200 according to the present disclosure, in conjunction with the prior art standard radiation apron 10 of FIG. 1.

Like the radiation shielding device of FIG. 3 through FIG. 5, the radiation shielding device 200 of FIG. 6 and FIG. 7 includes a first shielded portion 210 configured to cover and protect the right axilla, the outer quadrants of the right breast, and a portion of the right chest of a user, and a second shielded portion 212 configured to cover and protect the left axilla, the outer quadrants of the left breast, and a portion of the left chest of the user. The first shielded portion 210 and the second shielded portion 212 may further be configured to cover and protect a portion of the shoulders of the user and/or a portion of the back of the user.

The radiation shielding device 200 may further include a first sleeve 214 coupled to the first shielded portion 210 and a second sleeve 216 coupled to the second shielded portion 212. The first sleeve 214 and the second sleeve 216 each include radiation shielding material configured to cover and protect the proximal arms 46 of the user from radiation. In some implementations, a first adjustment strap 230 is coupled to the first sleeve 214 and a second adjustment strap 232 is coupled to the second sleeve 216 to enable the user to adjust the width of each sleeve opening.

As shown, the first shielded portion 210, the second shielded portion 220, the first sleeve 214, and the second sleeve 216 provide complete coverage to protect the axilla 44, and in this implementation, the full proximal arms 46 of the user. Since the user is normally facing the radiation scatter source during procedures, and radiation scatter comes mostly in an upward direction from below, this complete coverage of shielding material provides protection to the user that is not found in prior art designs, which leave openings in the underside of the proximal arms 46 and the axilla 44.

The radiation shielding device 200 may further include a third shielded portion 218 configured to cover and protect both the neck 48 and a portion of the chest 50 of a user. The third shielded portion 218 may cover the entire area left exposed by the neck opening 18 in the standard radiation apron 10, as shown in FIG. 1, while also providing thyroid protection in place of the thyroid guard 30 shown in FIG. 2. In this implementation, the third shielded portion 218 is integrally formed into the radiation shielding device 200. In other implementations, the third shielded portion 218 may be attached but fully removable from the radiation shielding device 200.

In some implementations, the radiation shielding device 200 uses shielding material in the first, second and third shielded portions 210, 212, 218 that attenuates ionizing radiation associated with medical imaging. This shielding material is enclosed in fabric, so the shielding material acts as a liner in the garment 200.

The radiation shielding device 200 further includes a plurality of lightweight material portions 220. The lightweight material portions 220 may include a first front lightweight material portion 222, a second front lightweight material portion 224, and a back lightweight material portion 226 configured to cover portions of the torso of the user. These lightweight material portions 222, 224, and 226 couple the first shielded portion 210 to the second shielded portion 212 and to the third shielded portion 218 to create the garment 200. In this implementation, the first sleeve 214 and the second sleeve 216 are formed only of shielded material and do not include lightweight material portions 220. In other implementations, the first sleeve 214 and the second sleeve 216 may include lightweight material portions, but only on the backs of the sleeves 214, 216, not on the parts of the sleeves 114, 116 that cover the underside of the proximal arms 46, which ensures that area is protected from radiation scatter.

The radiation shielding device 200 may be secured at the front with a closure 240, such as a hook and loop arrangement, buttons, snaps, zippers, or similar closure mechanisms. In some implementations, the first front lightweight material portion 222 overlaps the second front lightweight material portion 224, and the third shielded portion 218 overlaps the second shielded portion 212 when the closure 240 is fastened, as shown in FIG. 6. In some implementations, the closure 240 is adjustable such that the lightweight material portions 220 and the adjustable closure 240 enable modifications to the size and shape of the garment 200, allowing the user freedom of movement. The lightweight material portions 220 lighten the weight of the radiation shielding device 200, provide breathability to the garment, and allow the first shielded portion 210, the second shielded portion 212, and the third shielded portion 218 to stay in place as the user moves. In some implementations, the lightweight material portions 220 are formed of a mesh material, a flexible material, or a combination thereof. For example, the first front lightweight material portion 222 and the second front lightweight material portion 224 may be formed of a mesh material, and the back lightweight material portion 226 may be formed of a flexible material as depicted in FIG. 6 and FIG. 7.

Figure 8:
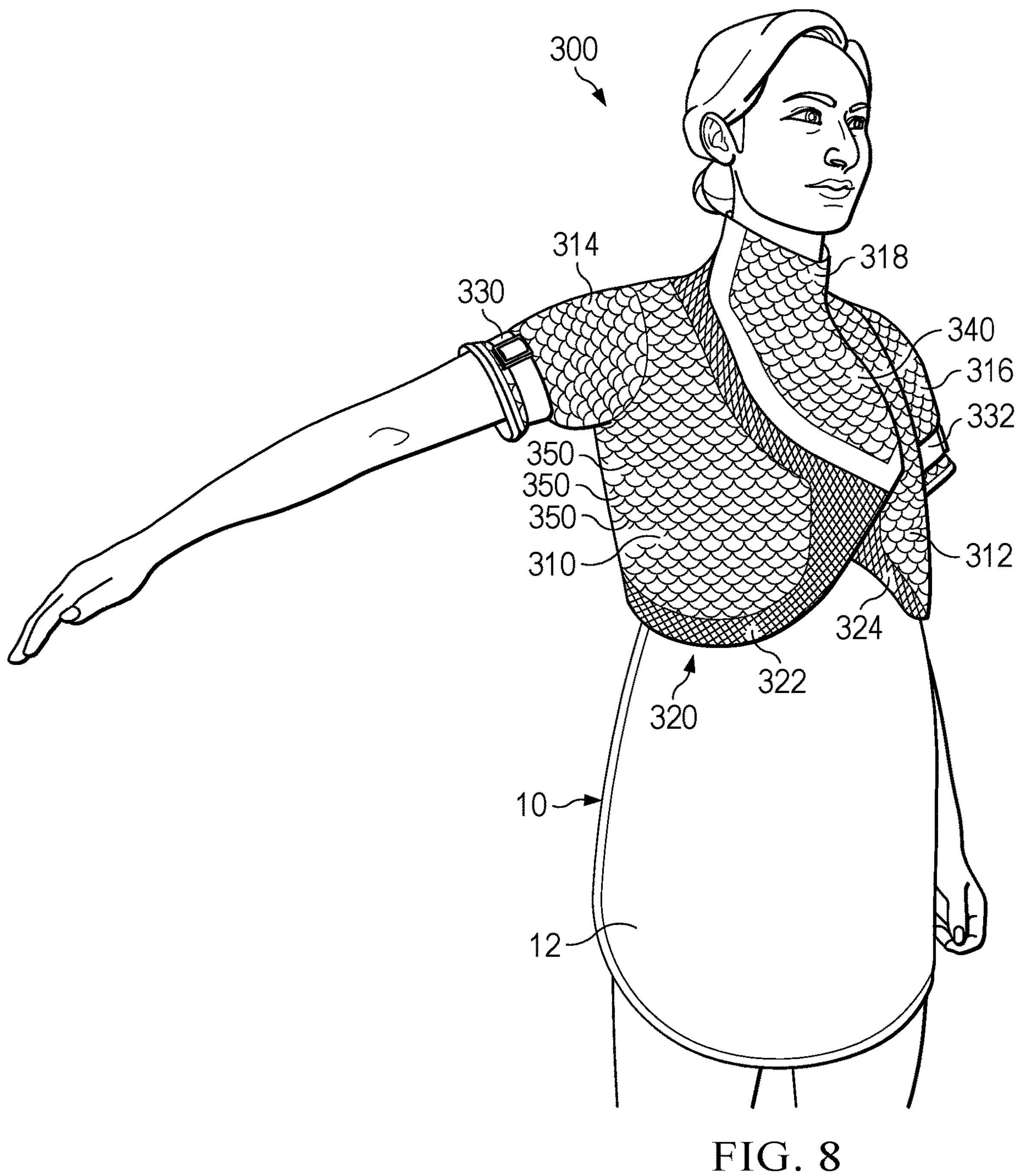
FIG. 8 illustrates a side perspective view of a user wearing yet another implementation of a radiation shielding device according to the present disclosure, in conjunction with the prior art standard radiation apron of FIG. 1.

FIG. 8 depicts a side perspective view of a user wearing yet another implementation of a radiation shielding device 300 according to the present disclosure, in conjunction with the prior art standard radiation apron 10 of FIG. 1. The radiation shielding device 300 of FIG. 8 is constructed in a similar manner to the radiation shielding device 200 of FIG. 6 and FIG. 7, except FIG. 8 depicts a different form of shielding material, shown with the enclosing fabric removed for clarity.

Like the radiation shielding device 200 of FIG. 6 and FIG. 7, the radiation shielding device 300 of FIG. 8 includes a first shielded portion 310 configured to cover and protect the right axilla, the outer quadrants of the right breast, and a portion of the right chest of a user, and a second shielded portion 312 configured to cover and protect the left axilla, the outer quadrants of the left breast, and a portion of the left chest of the user. The first shielded portion 310 and the second shielded portion 312 may further be configured to cover and protect a portion of the shoulders of the user and/or a portion of the back of the user.

The radiation shielding device 300 may further include a first sleeve 314 coupled to the first shielded portion 310 and a second sleeve 316 coupled to the second shielded portion 312. The first sleeve 314 and the second sleeve 316 each include radiation shielding material configured to cover and protect at least a portion of the proximal arms of the user from radiation, including the undersides of the proximal arms. In some implementations, a first adjustment strap 330 is coupled to the first sleeve 314 and a second adjustment strap 332 is coupled to the second sleeve 316 to enable the user to adjust the width of each sleeve opening.

The radiation shielding device 300 may further include a third shielded portion 318 configured to cover and protect both the neck 48 and a portion of the chest 50 of a user. The third shielded portion 318 may cover the entire area left exposed by the neck opening 18 in the standard radiation apron 10, as shown in FIG. 1, while also providing thyroid protection in place of the thyroid guard 30 shown in FIG. 2. In this implementation, the third shielded portion 318 is integrally formed into the radiation shielding device 300.

The radiation shielding device 300 further includes a plurality of lightweight material portions 320. The lightweight material portions 320 may include a first front lightweight material portion 322, a second front lightweight material portion 324, and a back lightweight material portion 326 (not shown) configured to cover portions of the torso of the user. These lightweight material portions 322, 324, and 326 couple the first shielded portion 310 to the second shielded portion 312 and to the third shielded portion 318 to create the garment 300.

The radiation shielding device 300 may be secured at the front with a closure 340, such as a hook and loop arrangement, buttons, snaps, zippers, or similar closure mechanisms. In some implementations, the first front lightweight material portion 322 overlaps the second front lightweight material portion 324, and the third shielded portion 318 overlaps the second shielded portion 312 when the closure 340 is fastened, as shown in FIG. 8. In some implementations, the closure 340 is adjustable such that the lightweight material portions 320 and the adjustable closure 340 enable modifications to the size and shape of the garment 300, allowing the user freedom of movement. The lightweight material portions 320 lighten the weight of the radiation shielding device 300, provide breathability to the garment, and allow the first shielded portion 310, the second shielded portion 312, and the third shielded portion 318 to stay in place as the user moves. In some implementations, the lightweight material portions 320 are formed of a mesh material, a flexible material, or a combination thereof. For example, the first front lightweight material portion 322 and the second front lightweight material portion 324 may be formed of a mesh material, and the back lightweight material portion 326 may be formed of a flexible material.

In the implementation shown in FIG. 8, to improve the wearability of the garment 300, the shielding material that forms the first, second and third shielded portions 310, 312, 318, and the shielding material on the sleeves 314, 316, is formed into small, overlapping segments 350 attached at one end to the garment 300. These segments 350 are sized to slide over each other as the user moves, while still providing radiation protection.

In other implementations, the present disclosure is directed to methods of radiation shielding by radiation shielding devices 100, 200, 300 worn in conjunction with standard radiation aprons 10. The method may comprise a user first putting on a standard radiation apron 10, then putting on a radiation shielding device 100, 200, 300 over the standard radiation apron 10. In another implementation, the method may comprise a user first putting on a radiation shielding device 100, 200, 300, then putting on a standard radiation apron 10 over the radiation shielding device 100, 200, 300.

Putting on the radiation shielding device 100, 200, 300 may comprise the user inserting one arm into the first sleeve 114, 214, 314, the user inserting the other arm into the second sleeve 116, 216, 316, and the user fastening the closure 140, 240, 340. The method may further comprise the user adjusting the adjustable straps 130, 132, 230, 232, 330, 332 on the sleeves 114, 116, 214, 216, 314, 316. The method may further comprise the user securing the third shielded device 118 into place on the garment 100.

It is to be understood the implementations are not limited to particular systems or processes described which may, of course, vary. For example, the radiation shielding devices 100, 200, 300 depicted and described herein may vary in form and structure, and the teachings of the present disclosure may be applied to any radiation shielding device designed to shield those portions of the upper body left exposed by standard radiation aprons.

It is also to be understood that the terminology used herein is for the purpose of describing particular implementations only, and is not intended to be limiting. As used in this specification, the singular forms "a", "an" and "the" include plural referents unless the content clearly indicates otherwise. As another example, "coupling" includes direct and/or indirect coupling of members.

Although the present disclosure has been described in detail, it should be understood that various changes, substitutions and alterations may be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

The invention claimed is:

1. A radiation shielding device comprising:

a first shielded portion configured to cover the right axilla and the outer quadrants of the right breast of a user with shielding material;

a second shielded portion configured to cover the left axilla and the outer quadrants of the left breast of a user with shielding material;

a first arm sleeve coupled to the first shielded portion and configured to cover an underside portion of a right proximal arm of a user with shielding material;

a second arm sleeve coupled to the second shielded portion and configured to cover an underside portion of a left proximal arm of a user with shielding material; and a plurality of lightweight material portions coupling the first shielded portion and the second shielded portion.

2. The radiation shielding device of claim 1, further comprising a third shielded portion adapted to cover a portion of the chest of a user with shielding material.

3. The radiation shielding device of claim 1, further comprising a third shielded portion adapted to cover a portion of the chest and the thyroid of a user with shielding material.

4. The radiation shielding device of claim 1, further comprising a thyroid shield adapted to cover a thyroid of a user with shielding material.

5. The radiation shielding device of claim 1, further comprising a first strap configured to adjust a width of the first arm sleeve and a second strap configured to adjust a width of the second arm sleeve.

6. The radiation shielding device of claim 1, wherein the plurality of lightweight material portions comprises a first front portion, a second front portion, and a back portion.

7. The radiation shielding device of claim 1, further comprising a closure.

8. The radiation shielding device of claim 7, wherein the closure adjustably fastens the first front lightweight portion to the second front lightweight portion.

9. The radiation shielding device of claim 7, wherein the closure adjustably fastens the third shielded portion to the second shielded portion.

10. The radiation shielding device of claim 1, wherein the shielding material of at least one of the first shielded portion, the second shielded portion, the first arm sleeve, and the second arm sleeve comprise small, overlapping segments of shielding material.

11. The radiation shielding device of claim 1, wherein the plurality of lightweight material portions comprises a mesh material, a flexible material, or a combination thereof.

12. The radiation shielding device of claim 1, wherein:

the first shielded portion and the first sleeve are configured to cover, without interruption, the right axilla, the outer quadrants of the right breast, and the underside portion of the right proximal arm of the user with shielding material; and the second shielded portion and the second sleeve are configured to cover, without interruption, the left axilla, the outer quadrants of the left breast, and the underside portion of the left proximal arm of the user with shielding material.

13. The radiation shielding device of claim 1, wherein the radiation shielding device is structured to be worn underneath or over a standard radiation apron.

14. A radiation shielding device, comprising:

a first shielded portion adapted to shield the right axilla and the outer quadrants of the right breast of a user from radiation, wherein the first shielded portion extends substantially vertically from the user's right shoulder down below the right axilla and extends substantially laterally from the outer quadrants of the right breast to the posterior of the right axilla;

a second shielded portion adapted to shield the left axilla and the outer quadrants of the left breast of a user from radiation, wherein the second shielded portion extends substantially vertically from the user's left shoulder down below the left axilla and extends substantially laterally from the outer quadrants of the left breast to the posterior of the left axilla;

a third shielded portion adapted to shield a portion of the chest and the thyroid of a user from radiation, wherein the third shielded portion extends substantially vertically from above the thyroid down to the middle of the chest of the user;

a first arm sleeve attached to the first shielded portion, the first arm sleeve adapted to shield at least an underside portion of a right proximal arm of a user from radiation;

a second arm sleeve attached to the second shielded portion, the second arm sleeve adapted to shield at least an underside portion of a left proximal arm of a user from radiation; and a plurality of lightweight material portions adapted to couple the first shielded portion, the second shielded portion, and the third shielded portion.

15. The radiation shielding device of claim 14, further comprising a first strap adapted to adjust a width of the first arm sleeve and a second strap adapted to adjust a width of the second arm sleeve.

16. The radiation shielding device of claim 14, wherein the plurality of lightweight material portions comprises:

a first front lightweight material portion coupled to the first shielded portion and the third shielded portion;

a second front lightweight material portion coupled to the second shielded portion and adapted to fasten to the third shielded portion; and a back lightweight material portion coupled to the first shielded portion and the second shielded portion.

17. The radiation shielding device of claim 14, wherein the plurality of lightweight material portions comprises:

a first front lightweight material portion coupled to the first shielded portion and adapted to fasten to the third shielded portion; and a second front lightweight material portion coupled to the second shielded portion and the third shielded portion; and a back lightweight material portion coupled to the first shielded portion and the second shielded portion.

18. The radiation shielding device of claim 14, wherein at least one of the first shielded portion, the second shielded portion, the third shielded portion, the first arm sleeve, and the second arm sleeve comprise small, overlapping segments of shielding material.

19. The radiation shielding device of claim 14, wherein the plurality of lightweight material portions comprises a mesh material, a flexible material, or a combination thereof.

20. The radiation shielding device of claim 14, further comprising a closure.

21. The radiation shielding device of claim 20, wherein the closure adjustably fastens the first front lightweight portion to the second front lightweight portion.

22. The radiation shielding device of claim 20, wherein the closure adjustably fastens the third shielded portion to the second shielded portion.

23. The radiation shielding device of claim 14, wherein:

the first shielded portion and the first sleeve are configured to cover, without interruption, the right axilla, the outer quadrants of the right breast, and the underside portion of the right proximal arm of the user with shielding material; and the second shielded portion and the second sleeve are configured to cover, without interruption, the left axilla, the outer quadrants of the left breast, and the underside portion of the left proximal arm of the user with shielding material.

24. The radiation shielding device of claim 14, wherein the radiation shielding device is structured to be worn underneath or over a standard radiation apron.

* * * * *